United States Patent [19]

Eberle et al.

[11] Patent Number: 5,368,037
[45] Date of Patent: Nov. 29, 1994

[54] ULTRASOUND CATHETER

[75] Inventors: Michael J. Eberle, Fair Oaks; Gary P. Rizzuti, Shingle Springs; Horst F. Kiepen, Georgetown, all of Calif.

[73] Assignee: Endosonics Corporation, Rancho Cordova, Calif.

[21] Appl. No.: 12,251

[22] Filed: Feb. 1, 1993

[51] Int. Cl.⁵ .................. A61B 8/12; H04R 17/00
[52] U.S. Cl. .................. 128/662.06; 29/25.35
[58] Field of Search .................. 128/660.03, 660.1, 662.05–662.06, 128/4; 29/25.35

[56] References Cited

U.S. PATENT DOCUMENTS

| | | | |
|---|---|---|---|
| 3,605,723 | 9/1971 | King et al. | 128/662 |
| 3,827,115 | 8/1974 | Bom | 29/25 |
| 3,938,502 | 2/1976 | Bom | 128/2 |
| 4,191,193 | 3/1980 | Seo | 128/675 |
| 4,211,949 | 7/1980 | Brisken et al. | 128/660 |
| 4,237,900 | 12/1980 | Schulman et al. | 128/630 |
| 4,274,423 | 6/1981 | Mizuno et al. | 128/675 |
| 4,325,257 | 4/1982 | Kino et al. | 73/626 |
| 4,456,013 | 6/1984 | De Rossi et al. | 128/675 |
| 4,505,156 | 3/1985 | Questo | 73/626 |
| 4,576,177 | 5/1986 | Webster, Jr. | 128/660 |
| 4,582,067 | 4/1986 | Silverstein et al. | 128/662.06 X |
| 4,589,419 | 5/1986 | Laughlin et al. | 128/663 |
| 4,641,657 | 2/1987 | Ellis | 128/660 |
| 4,665,925 | 5/1987 | Millar | 128/344 |
| 4,671,293 | 6/1987 | Shaulov | 128/660 |
| 4,771,782 | 9/1988 | Millar | 128/637 |
| 4,771,788 | 9/1988 | Millar | 128/661 |
| 4,794,931 | 1/1989 | Yock | 128/662 |
| 4,817,616 | 4/1989 | Goldstein | 128/662.06 |
| 4,841,977 | 6/1989 | Griffith et al. | 128/662 |
| 4,917,097 | 4/1990 | Proudian et al. | 128/661.01 X |
| 4,951,677 | 8/1990 | Crowley et al. | 128/662 |
| 5,046,503 | 9/1991 | Schneiderman | 128/662 |
| 5,081,993 | 1/1992 | Kitney et al. | 128/662.06 X |
| 5,117,831 | 6/1992 | Jang et al. | 128/662.06 |
| 5,167,233 | 12/1992 | Eberle et al. | 128/662 |
| 5,174,296 | 12/1992 | Watanabe et al. | 128/662.06 |
| 5,186,177 | 2/1993 | O'Donnell et al. | 128/662.06 |
| 5,199,437 | 4/1993 | Langberg | 128/662.06 |

FOREIGN PATENT DOCUMENTS 1402192  8/1975  United Kingdom .

OTHER PUBLICATIONS

"Signal Enhancement for Automatic Identification of Arterial Wall Echos from an Intravessel Scanner", Martin et al., Ultrasound in Medicine, vol. 4 (New York 1978), pp. 417–431.

"Polyvinylidene Fluoride Acoustic Transducers and Imaging Arrays", Weinstein, Ph.D. Thesis, Stanford University, Oct. 1982.

"On the Generation of High–Frequency Acoustic Energy with Polyvinylidene Fluoride", Swartz et al., IEEE T–SU #27, Nov. 1980.

"Piezoelectric & Ferroelectric Properties of P(VD–TrFE) Copolymers & Their Application to Ultrasonic Transducers", Ohigashi et al., Ferroelectrics, vol. 60, pp. 263–276, 1984.

"Ultrasonic Imaging Using Arrays", Macovski, Proc. IEEE, vol. 67, #4, pp. 484–495, Apr. 1979.

"An Ultrasonic Catheter for Intravascular Measurement of Blood Flow: Technical Details", Martin et al., IEEE, vol. SU–27, No. 6, pp. 277–286, Nov. 1980.

"Acoustic Waves: Devices, Imaging, and Analog Signal Processing", Kino, 1987, pp. 554–559.

"Biomedical Ultrasonics", Wells, 1977, pp. 49–55.

Primary Examiner—Francis Jaworski
Attorney, Agent, or Firm—Leydig, Voit & Mayer, Ltd.

[57] ABSTRACT

An ultrasound catheter is disclosed for providing substantially real-time images of small cavities. The ultrasound catheter is characterized by separate and distinct materials for backing the transducers and for carrying the electronics components. The separate materials comprise an electronics carrier meeting the requirements for holding the integrated circuitry of the ultrasound device and a backing material displaying superior characteristics relating to reducing ringing and minimizing the effect of other sources of signal degradation in the transducer assembly. Also, in accordance with the present invention, a technique is described for connecting the conductor lines of the separate transducer assembly and electronics body.

17 Claims, 5 Drawing Sheets

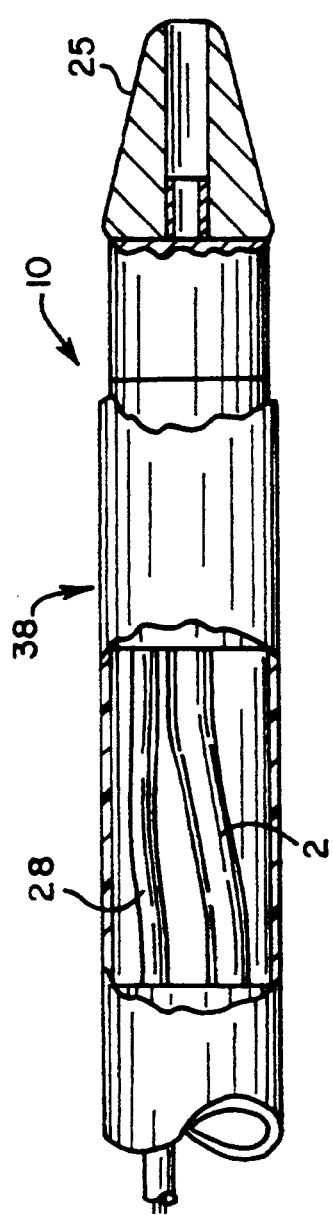
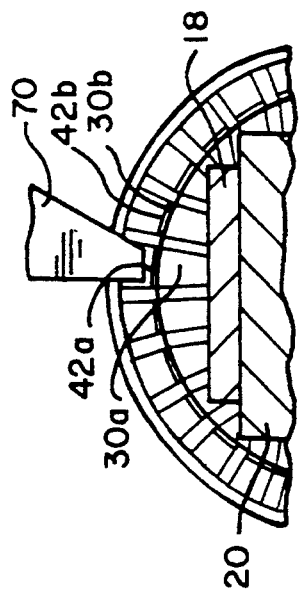
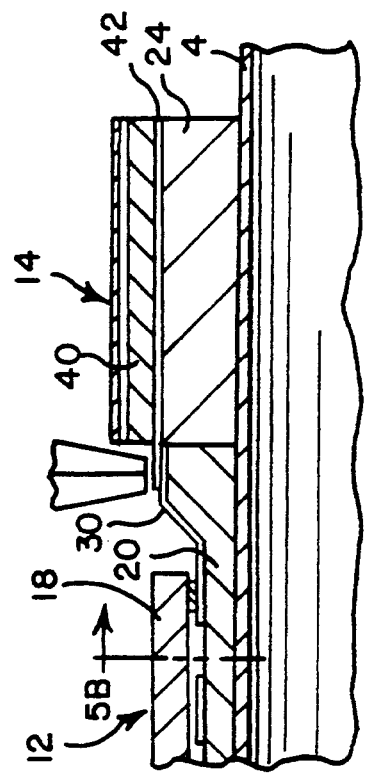

ULTRASOUND CATHETER

INCORPORATION BY REFERENCE

The applicants hereby incorporate by reference the description of an "Apparatus and Method for Imaging Small Cavities" described in Proudian et al. U.S. Pat. No. 4,917,097 and the description of a "Dilating and Imaging Apparatus" described in Eberle et al. U.S. Pat. No. 5,167,233.

FIELD OF THE INVENTION

The present invention relates generally to the field of ultrasonic imaging, and more particularly to ultrasonic imaging to determine various characteristics of relatively small cavities and surrounding fluids and structures.

BACKGROUND OF THE INVENTION

Diagnosis and treatment of fully or partially blocked arteries of the heart is essential in the medical profession's endeavor to prevent heart attacks. Physicians have successfully prevented heart attacks arising from artery blockage caused by the build-up of plaque upon the walls of the coronary arteries through the use of percutaneous transluminal coronary angioplasty (PTCA, commonly referred to as "balloon angioplasty"). Balloon angioplasty involves carefully threading a catheter into the affected portion of the artery. After the balloon portion is determined to be properly positioned in the artery, the physician inflates the expandable portion of the catheter in order to broaden the blocked or narrowed passage in the blood vessel caused by the deposition of plaque upon the artery wall.

The desirability of using an imaging device to produce treatment and diagnostic quality images of small enclosed areas such as human blood vessels on a diagnostic video display device is unquestioned. It is known to use a very small ultrasonic imaging device mounted at the end of a catheter to produce a real-time image of the internal walls of a coronary artery. This device is referred to herein as an ultrasound catheter.

In the known ultrasound catheters, the same material is used for the electronics carrier upon which a set of electronic components are mounted and for the backing material for the transducer assembly. A drawback to the known ultrasound catheters is the difficulty in finding a carrier/backing material which provides the physical and acoustic qualities desired for advantageous use as the carrier for the electronics and the backing material for a transducer assembly comprising a highly sensitive transducer material.

The known ultrasonic catheter structure, though providing the advantage of design and construction simplicity, exhibits certain drawbacks attributable to the particular and mutually incompatible requirements for the backing material and the electronics carrier. It is desirable that the electronics carrier for the electronics body be rigid and capable of withstanding the elevated temperatures produced by the electronics. However, the known electronics carrier materials which satisfy the requirements for the electronics body are not suitable backing materials for the presently preferred transducer assemblies comprising highly sensitive lead zirconate titanate (PZT) composites.

When the new, more sensitive PZT composites are used with the known electronic carrier material as the backing material for the transducer, unwanted ringing occurs in the transducer assembly when an acoustic signal is received or transmitted by the catheter. The signal produced by the ringing reduces the quality of the signal transmitted by the transducer assembly and limits the foreseeable advantages of utilizing the more sensitive transducer materials in ultrasonic catheters. The decreased signal quality attributed to the ringing limits the image quality provided by an ultrasound catheter. The limited image quality restricts the usefulness of the ultrasound catheter for clinical and diagnostic imaging.

In known ultrasound catheters the transducer electrodes are coupled to the transducer layer through a capacitive glue layer. As was previously mentioned, PZT composites having a relatively high degree of sensitivity to acoustic signals are being considered for replacement of the previously used, less sensitive, ferroelectric polymer transducer materials. While the PZT composites exhibit superior sensitivity in comparison to the ferroelectric copolymers, they also have a higher dielectric constant. The reduced impedance (or increased capacitance) associated with the new PZT composites significantly negates the improved signal sensitivity provided by the PZT composites when coupled to the transducer electrodes through the capacitive glue layer.

SUMMARY OF THE INVENTION

It is an object of the present invention to provide a superior virtually real-time ultrasonic image of relatively small cavities and their surrounding tissues than previously obtainable in the prior art.

It is a further object to provide enhanced sensitivity to reflected signals from the walls of a cavity in order to provide improved image resolution.

It is a further object of the invention to meet the other objectives and maintain or reduce ringing and other sources of noise in a signal transmitted or received by the transducer assembly and to thereby provide a clearer image of a cavity.

It is yet another object of the present invention to provide a means for more easily fabricating the very small transducer elements of the transducer assembly of an ultrasound catheter.

It is yet another object of the present invention to provide a means for forming the very small transducer elements for the ultrasound catheter to very close tolerances.

It is another object of the present invention to provide desirable carrier/backing materials for the electronics body and transducer assembly of an ultrasound catheter.

It is yet another object of the present invention to provide a means for joining the conductor lines of the electronics body to the conducting electrodes of the transducer assembly in order to provide a signal path between the separately fabricated sections containing the integrated circuits and the transducer assembly of an ultrasound catheter.

The above objects are met by a catheter probe assembly of the present invention comprising a multi-sectioned body for insertion into a cavity. The multi-sectioned body is characterized by separate and distinct carrier/backing materials for an electronics body and a transducer assembly. The present invention comprises a probe assembly for an ultrasound catheter generally of the type described in Proudian deceased et al. U.S. Pat.

No. 4,917,097 and Eberle et al. U.S. Pat. No. 5,167,233 for producing substantially real-time images of small cavities and their surrounding tissue.

The transducer assembly, comprising an array of transducers is mounted upon a first section of the multi-sectioned body. The transducer array transmits ultrasonic acoustic waves to the cavity and generates electrical signals in response to reflected ultrasonic acoustic waves received by the transducers.

The backing material for the transducer assembly is specifically selected for its characteristic low acoustic impedance and high absorption. The low acoustic impedance backing material absorbs signals coupled into the backing material and reduces the presence of ringing in the transducer assembly. In addition, a set of transducer electrodes are directly bonded to the transducer material thereby eliminating a capacitive glue layer previously associated with the transducer circuits.

Integrated circuits are mounted upon a second section of the multi-sectioned body. The second section, acoustically isolated from the first section, comprises a carrier material having a low thermal expansion coefficient. The integrated circuits receive a set of first electrical signals from the transducer array by means of electrical conductors interconnecting the transducer assembly electrodes and the pads of the integrated circuits. The electrical conductors are also used to transmit excitation signals from the integrated circuits to the transducer assembly. The integrated circuits convert the received first electrical signals into a second set of electrical signals. Then the integrated circuits transmit the second set of signals to a signal processor located outside the environment of the cavity by means of a cable.

The unique, multi-sectioned, structure of the probe assembly enables the designer of the probe assembly to separately select a material exhibiting the preferred structural and acoustic characteristic for the carrier of the integrated circuit components and the backing material for the transducer elements.

In order to prevent damage to the components of both the transducer assembly and the electronics body, these two portions of the ultrasound catheter probe assembly are separately manufactured and linked during the final stages of fabrication of the ultrasonic catheter.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

FIGS. 5a and 5b illustratively depict an alternative embodiment of the ultrasound catheter wherein the conducting electrodes in the transducer assembly extend beyond the backing material and the transducer material;

FIG. 6 is a side cross-sectional view of the tip of a catheter illustrating the electronics body, transducer assembly, and nose assembly of an ultrasound diagnostic imaging catheter embodying the present invention;

While the invention will be described in connection with a catheter used for angioplasty, it will be understood that it is not intended to be limited to such use. On the contrary, the invention is intended to cover all applications which may require imaging in a small cavity. An example of such an alternative would be the use of the present invention on a catheter without the balloon. In such a case, the catheter acts as a diagnostic or monitoring device. Another specific alternative use of the present invention is for measuring blood flow rates using Doppler sound imaging in conjunction with the present invention. The present invention may also be used to produce internal images of a number of ducts within a body such as the monitoring of gall stones in the bile ducts and for examination and treatment in the area of urology and gynecology. Another example of an application of the present invention is the use of the ultrasound catheter for providing an image of a vessel or duct during application of laser treatment or during the removal of plaque from the walls of a vessel during an antherectomy procedure.

Furthermore, this invention may be applied to other types of transducer array configurations which will be known to those of ordinary skill in the art in view of the description of the invention and the accompanying descriptions of various embodiments of this invention contained herein.

DETAILED DESCRIPTION OF THE PREFERRED EMBODIMENT

Though the present invention concerns the structure of the carrier/backing material for the electronics body and transducer assembly and changes to the physical layers of the transducer assembly, the invention is intended to be incorporated in general into an ultrasound catheter imaging system of the type described in Proudian, deceased et al. U.S. Pat. No. 4,917,097 the teachings of which are incorporated herein by reference.

Figure 1:
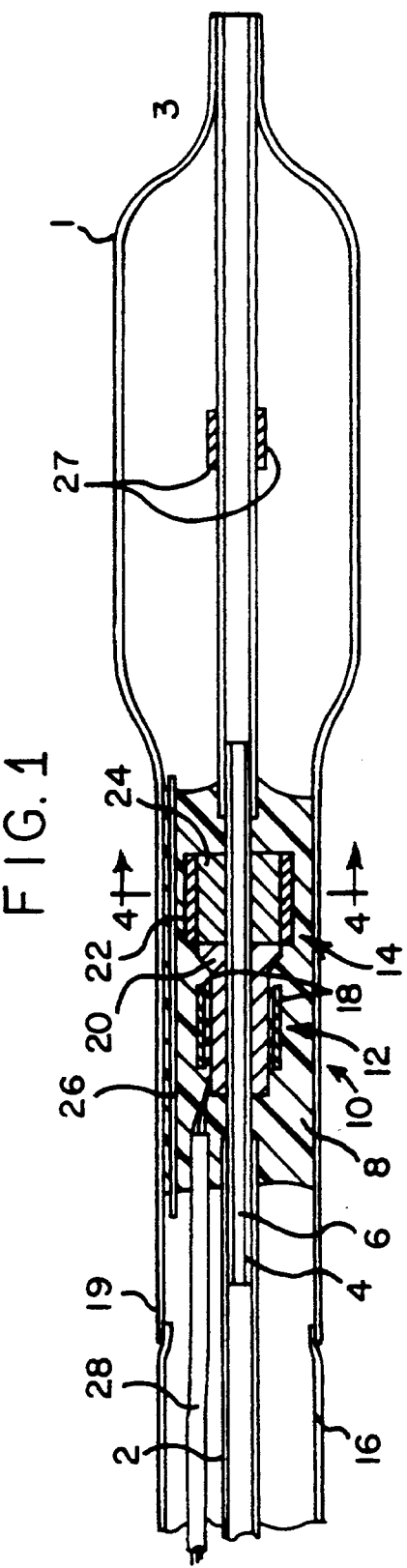
FIG. 1 is a side cross-sectional view of the tip of a catheter illustrating the electronics body, the transducer assembly, and the balloon section of a balloon angioplasty ultrasound imaging catheter embodying the present invention.

A cross-sectional view of a catheter embodying the present invention is illustratively depicted in FIG. 1. The catheter shown in FIG. 1 carrying a balloon 1 is of the type which is generally used for angioplasty; however, the invention can be used in conjunction with a number of catheter designs such as those illustratively depicted in FIGS. 6, 7 and 8 to provide diagnostic images and deliver treatment to small cavities of the body. Conventional guide wire lumens 2 and 3 are telescopically fitted over a mating radiopaque guide wire lumen 4 forming a central bore 6 for a catheter guide wire during a normal catheterization procedure. An encapsulant 8 composed of an epoxy material secures an imaging device 10 comprising the electronics body 12 and the transducer assembly 14 to the end of a catheter shaft 16. The imaging device 10 in accordance with the present invention contains a multi-sectioned body comprising separate and distinct materials for a carrier 20 and a transducer backing material 24. The encapsulant 8 protects and insulates a set of integrated circuits (IC's) 18 mounted upon the carrier 20. In the preferred embodiment of a balloon angioplasty device embodying the present invention, the imaging device 10 is positioned within a proximal sleeve 19 of the balloon 1.

The transducer assembly 14, described hereinafter in greater detail in conjunction with FIG. 3, generally comprises a set of transducer elements 22. The transducer elements 22 are supported in a cylindrical shape about the backing material 24. However, other transducer element configurations will be known to those skilled in the area of transducer devices in view of the present description and in view of the state of the art.

Continuing with the description of FIG. 1, the balloon 1 is positioned adjacent the imaging device 10 and is isolated from ambient conditions by sealing the two ends of the balloon 1 to the catheter shaft 16 and the lumen 3 in a conventional manner. A tube 26 is embedded within the encapsulant 8 for communicating a fluid between the balloon 1 and an inflation source. Within the expandable portion of the balloon 1 and attached to the lumen 3 is a radiopaque marker band 27 to assist in locating the position of the catheter on a fluoroscope.

A cable 28 comprising an inner and outer set of wires carries electronic data and control signals between the IC's 18 and a control station computer. Each inner wire in the cable 28 is formed from a solid conductor protected by an insulating coating. The outer wires are spiraled a number of times around the cable 28 in order to shield the signals carried by the inner wires of the cable 28. Preferably, the cable is coated with an insulating material.

Figure 2:
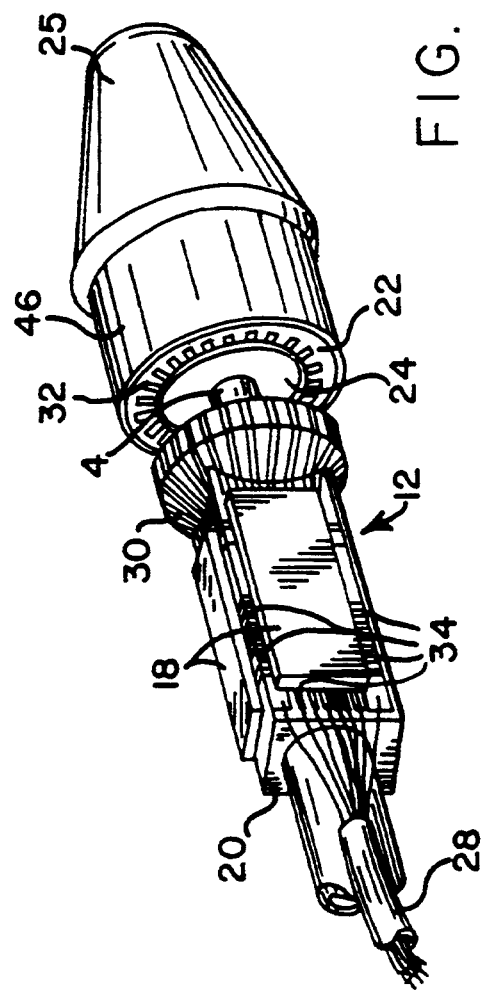
FIG. 2 is a perspective view of the tip of a partially constructed diagnostic imaging catheter prior to joining the signal paths between the separated electronics body and transducer assembly.

Turning now to FIG. 2, a perspective view is provided of the tip of a partially constructed diagnostic imaging catheter 10 prior to joining the signal paths between the separated electronics body 12 and transducer assembly 14 in order to show the distinct first and second portions of the imaging device 10 comprising the transducer assembly 14 and the electronics body 12. To aid the description of the imaging device 10, the proximal sleeve 19 and the epoxy encapsulant 8 covering the imaging device 10 have been removed to expose the integrated circuit chips 18 and associated electronic constructions. A nose cone 25 provides a blunted lead surface for the ultrasound imaging catheter in order to prevent damage to a vessel as the catheter is guided through the vessel.

The radiopaque guide wire lumen 4, visible within a patient by means of a fluoroscope, aids in the positioning of the catheter. The radiopaque guide wire lumen 4 also holds both the electronics body 12 and the transducer assembly 14. The outer diameter of the radiopaque guide wire lumen 4 is approximately 0.5 millimeters. The radiopaque guide wire lumen 4 provides the additional function of acting as a guide for precisely positioning the electronics body 12 and transducer assembly 14 in order to mate a set of 64 conductor lines 30 from the IC's 18 mounted upon the electronics body 12 to a set of 64 transducer contacts 32 of the transducer assembly 14 in a manner shown in FIG. 3. In order for the radiopaque guide wire lumen 4 to assist in mating the above described components of the imaging device 10, the gap between the radiopaque guide wire lumen 4 and both the carrier 20 and the backing material 24 must be very small and should not be greater than approximately 25 $\mu$m. This minimized gap ensures proper radial alignment of the conductor lines 30 and transducer contacts 32.

In order to physically place the IC's 18 onto the carrier 20, the four IC's 18 are of an inverted chip design known to those skilled in the area of the semiconductor chip fabrication art and are bonded to a set of conductive pads 34 formed on the carrier 20. The conductive pads 34 interconnect the IC's 18 to their neighboring chips and provide a connection between the IC's 18 and the cable 28 that communicatively couples the IC's 18 to a signal processor located outside the patient. The pads also connect the IC's 18 to the conductor lines 30. The conductor lines 30 link the IC's 18 to a set of 64 electrodes that define the transducer elements in the transducer assembly 14.

Each of the IC's 18 has 16 channels associated with 16 transducer elements defined by 16 transducer electrodes in the transducer assembly 14. Each of the four IC's 18 is responsible for sequentially transmitting and receiving electrical signals in the ultrasonic frequency range on one or more of its 16 channels linked by conductor lines 30 to an associated transducer element in the transducer assembly 14. The four IC's 18 provide a multiplexing function that distributes excitation pulses from a signal processor to one or more of the transducer elements. At any given time one or more of the 16 channels on each of the IC's 18 is free to be excited by an excitation signal or to receive reflections or echoes by means of activation control signals stored on the IC's 18. The electrical signals generated from the reflections impinging on the active transducer elements are amplified and sent via the transmission cable line 28 to the external signal processor.

Figure 3:
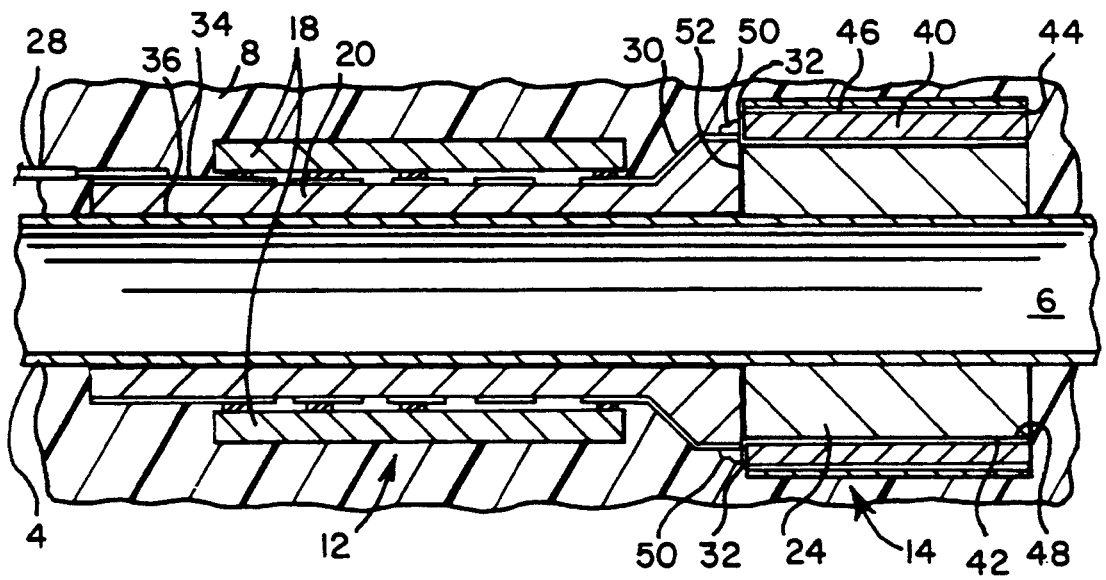
FIG. 3 is a detailed side cross-sectional view of the tip of the imaging device portion of the catheter showing the composition of the imaging device.

Turning to FIG. 3 a detailed side cross-sectional view of the imaging portion of the catheter of FIG. 1 is illustrated to show the structure and materials of the imaging device 10. In this drawing the electronics body 12 and the transducer assembly 14 are shown in their mated state as they would exist in the final construction of the imaging catheter. Though the layers of the transducer assembly are shown in detail in FIG. 3 it will be helpful to refer to FIG. 4, a cross section view of the transducer assembly taken along line 4—4 of FIG. 2, during the description of the ringed layers of the transducer assembly 14.

The carrier 20 is bonded to the radiopaque guide wire lumen 4 by means of a glue layer 36 comprising any commercially available medical grade cyanoacrylate epoxy. One may substitute any material or structure that satisfactorily immobilizes the electronics body 12 for the glue layer 36. As previously mentioned the space between the radiopaque guide wire lumen 4 and the carrier 20 filled by the glue layer 36 must be very small in order for the radiopaque guide wire lumen 4 to assist in the matching of the electrical contacts between the electronics body 12 and the transducer assembly 14.

The carrier 20 in the preferred embodiment of the invention is formed from a rigid, strong material having a low thermal expansion coefficient. The carrier 20 must be capable of withstanding temperatures in excess of 200 degrees Celsius to which the electronics body 12 is subjected during the process of bonding the set of IC's 18 to the carrier 20. Furthermore, during operation of the ultrasound catheter, self-heating of the IC's 18 may cause expansion of the carrier 20. If the thermal expansion of the carrier 20 is too great, shear forces exerted by the carrier 20 upon the conductive pads 34 create a substantial risk of failure of the electrical connection between the contacts of the IC's 18 and the conductor lines 30. Aluminum oxide ($Al_2O_3$) possesses the aforementioned desired characteristics for the carrier 20; however, other suitable substitutes for this material are well known to those skilled in the art of hybrid circuits. Aluminum oxide is also characterized by a very high acoustic impedance (approximately 40 MRayls) and relatively low loss. As will be explained below, these acoustical properties make Aluminum oxide a poor candidate for use as the transducer backing material for applications involving highly sensitive transducer elements.

An encapsulant 8 is applied to the outer surface of the electronics body 12 in order to provide a more cylindrical shape to the catheter assembly and to insulate the electronic circuitry. The encapsulant 8 generally comprises any commercially available medical grade UV-curable acrylic. In order to guard against contamination of the blood and possibly electrical shock, the outside of the electronics body may be covered by a protective layer. The protective layer is made of, for example, parylene. Other suitable materials for the protective layer will be known to those skilled in the art of ultrasound catheters or other medical instruments which are inserted within the body. The protective layer consists of the proximal sleeve 19 in the balloon angioplasty catheter shown in FIG. 1 or a sheath 38 in the case of a diagnostic imaging catheter such as the one illustrated in FIG. 6.

Turning to the transducer assembly 14 and its related structures, the backing material 24 for the transducer assembly 14 is preferably formed from a material characterized by a relatively low acoustic impedance (<10 MRayls) and high loss coefficient (on the order of 20 to 40 dB/mm). This is necessitated by the use of highly sensitive transducer materials such as the PZT composites used for a transducer material 40 whose superior signal sensitivity is otherwise negated by the ringing effect caused by a backing material having a high acoustic impedance and low loss. For this reason, Aluminum oxide is not a preferred material for the backing material 24 for the transducer assembly 14. Instead, a separate and different material is used to form the backing material 24 for the ultrasound catheter of the present invention. A preferred material for the backing material 24 is an epoxy resin filled with either rubber particles or glass microspheres. An example of such a resin is "light-weld" 183-M by Dymax Corp., Torrington, Conn. Other suitable materials having low acoustic impedance and high loss will be known to those of ordinary skill in the art of ultrasound imaging. Although air is an ideal backing material, transducer assemblies using an air backing are difficult to achieve in practice.

Thus, the ultrasound catheter of the present invention is characterized by an imaging device 10 having separate and distinct carrier/backing materials that exhibit greatly contrasting characteristics. The two distinct materials provide desirable structural and acoustical characteristics for satisfying the dissimilar requirements for the electronics body 12 and the transducer assembly 14.

Figure 4:
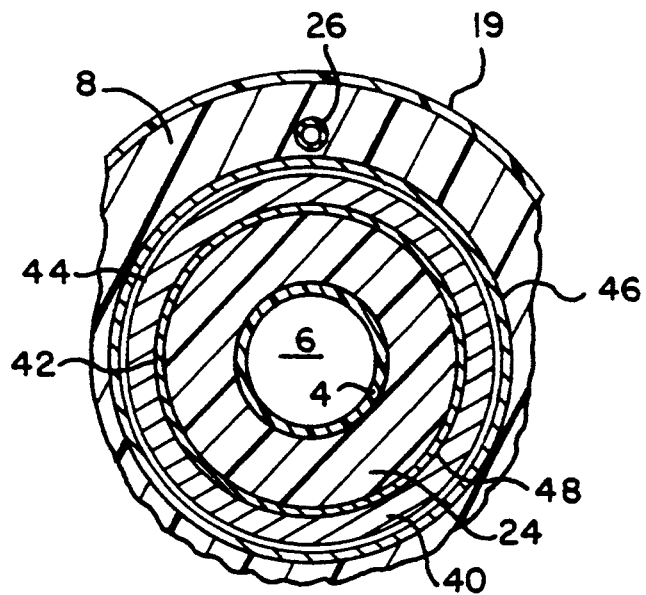
FIG. 4 is a cross-sectional view of the transducer assembly taken along line 4—4 in FIG. 1.

In the preferred method of making the transducer assembly 14, the outer layers of the transducer assembly 14 are separately manufactured as a planar sheet. They comprise a first set of 64 conducting electrodes 42, the transducer material 40, a continuous layer conducting electrode 44, and a matching layer 46. After the layers are fabricated, the planar sheet of transducer elements 22 is wrapped around the backing material 24 and bonded by means of a glue layer 48. Depending on the mechanical and acoustic properties of the transducer assembly 14, physical isolation of the transducer elements 22 from one another may be desirable. Since a uniform distribution of each of the transducer elements 22 is desired, the outer diameter of the backing material 24 must be manufactured within very close tolerances so that the ends of the planar sheet of transducer elements, when joined to form a cylinder around the backing material 24, meet with minimal gap or overlap. Alternatively, the planar transducer assembly 14 may be formed into a cylinder of exact outer diameter concentrically around the radiopaque lumen 4 and the gap between the lumen 4 and the transducer assembly 14 is filled with the backing material 24. This ensures that the spacing between the transducer array elements at the opposite ends of the cylindrically wrapped planar sheet have the same spacing as the other transducer array elements. It is believed that the error in the circumference of the transducer sheet, when wrapped around the lumen 4, should be less than (plus or minus) 8 $\mu$m. Furthermore, the inner diameter of the backing material 24 must closely match the outer diameter of the radiopaque guide wire lumen 4 in order to facilitate the mating of electrical contacts between the electronics body 12 and the transducer assembly 14. The concentric rings comprising the afore-described layers of the transducer assembly 14 are illustratively depicted in FIG. 4 showing a cross-sectional view of the transducer assembly taken on line 4—4 of FIG. 1.

An advantage of the planar sheet transducer element fabrication method is the absence of capacitive glue layers previously present between the transducer material 40 and each of the conducting electrodes 42 and 44. If the capacitive glue layer remained in the presently described ultrasound catheter, an increased capacitance attributable to the higher dielectric constant of the PZT composite transducer material 40 would negate the improved signal sensitivity of the preferred transducer material.

There are several other advantages to the sheet approach to fabricating the transducer array. Fabrication on a flat surface is easier than on a curved, cylindrical surface. This is especially important in transducer assemblies wherein the transducer material 40 must be separated (or diced) in order to form the transducer material on the continuous conducting electrode 44 as individual elements instead of a continuous sheet. The capability of fabricating the transducer material 40 as individual elements is an important factor when choosing a particular fabrication method in view of the desirability of low cross-talk (less than $-30$ dB), which may necessitate such a separation of elements. Some of the possible manufacturers of the planar sheets comprising the transducer elements are: Precision Acoustic Devices, Fremont, Calif.; Acoustic Imaging, Phoenix, Ariz.; Echo Ultrasound, Lewistown, Pa.; Vermon S. A., Tours, France; and Imasonic, Besancon, France.

After the transducer assembly 14 has been formed, it may be desirable for the transducer material to be polarized by means of a high voltage on the order of 5,000 Volts applied between the first set of conducting electrodes 42 and the continuous conducting electrode 44. Therefore, it is desirable to perform the polarization procedure on a separated assembly to isolate the transducer assembly 14 from the electronics body 12 since application of such a high voltage to the IC's 18 would destroy the electronic circuitry of the IC's 18.

The layer of glue 48 bonds the backing material 24 to the first set of conducting electrodes 42 spaced evenly about the circumference of the backing material 24. The first set of conducting electrodes 42 defines the individual transducer elements in the transducer array. The first set of conducting electrodes 42 is attached to the set of 64 transducer contacts 32. Connection material 50 electrically couples each one of the transducer contacts 32, corresponding to a single transducer element, to a corresponding one of the conductor lines 30, thereby providing an electronic signal path between the transducer elements 22 and the IC's 18. The connection material comprises any of several known suitable conductors such as silver or gold loaded epoxy droplets, solder or gold bumps, or solder tape.

There are other connection schemes for joining the conducting electrodes 42 to the conductor lines 30. FIGS. 5A and 5B illustratively depict an alternative embodiment of the ultrasound catheter wherein copper conducting electrodes 42 of the transducer assembly 14 extend beyond the backing material 24 and the transducer material 40. The portion of the conducting electrodes 42 extending beyond the backing material 24 and overlapping the conductor lines 30 when the transducer assembly 14 is joined to the electronics body 12 facilitates the use of a well known gap welder to fuse the individual conductor lines 30 to the corresponding conducting electrodes 42.

FIG. 5A shows a cross-sectional view of a partially constructed ultrasound catheter to show the above described connection scheme. The use of a gap welder eliminates the need to deposit individual drops of solder material 50 as shown in FIG. 3. The elimination of solder droplets potentially simplifies the design of the electronics carrier 20 that may otherwise require scalloping of the carrier at the end proximate the transducer assembly 14 in order to facilitate proper deposition of the droplets to fuse the conductor lines 30 and the transducer contacts 32. Other advantages of this connection scheme include better bonding of the conductors, simpler assembly techniques, and enhanced mechanical stability.

Another advantage of the connection scheme portrayed in FIGS. 5A and 5B is the potential to automate the process of bonding the conducting electrodes 42 to the conductor lines 30. As shown in the cross-sectional view of a partially assembled ultrasound catheter assembly in FIG. 5B, the conductor lines 30 are matched to the conducting electrodes 42. Next, a tip 70 of a gap welder is placed above one of the matched lines. The tip 70 presses a conducting electrode 42a to a corresponding conductor line 30a. A low voltage, high electrical current passes between the electrodes of the tip 70. The electrical current fuses the conducting electrode 42a to the conductor line 30a. Next, the catheter assembly is rotated so that a next matched set of lines (42b and 30b) is below the tip 70 and the welding process is repeated. The welding continues until all the lines have been fused.

Returning now to ultrasound imaging device in FIG. 3, there exists a range of suitable transducer materials which can be used to transduce electrical energy into acoustic energy and vice versa in the Megahertz frequency range. In the preferred embodiment of the present invention, the efficiency rating of the transducer material, expressed in terms of the coupling coefficient $k_t$, is high (greater than 50%); the bandwidth should be high (greater than 50% of center frequency); there should be good matching among the transducer elements; there should be low insertion loss (less than −40 dB); and the center frequency should be around 20 MHz. Therefore, in the preferred embodiment of the present invention, the transducer material 24 is any one of many known suitable PZT composites. A summary of the properties of the PZT composites is provided in *Acoustic Waves: Devices, Imaging, and Analog Signal Processing*, by Professor Gordon S. Kino, Prentice-Hall, Inc., 1987 at pages 554 and 555. Generally, these composites may be damaged by temperatures exceeding 75° Celsius and could not be present when the bonding of the IC's 18 to the carrier 20 occurs.

The radial thickness of the transducer layer 40 is preferably one-half wavelength thickness or an odd multiple of half wavelengths of the intended center operating frequency of the ultrasound catheter. As explained in Biomedical Ultrasonics, at page 53, this enables the transducer to resonate at the center operating frequency of the ultrasound catheter. In the present embodiment, the radial thickness of the transducer material 24 is approximately 0.1 millimeters.

In order to take advantage of the superior signal sensitivity of transducers formed from PZT composites, the backing material 24 must have a low acoustic impedance. Therefore, the aluminum oxide carrier 20 having a high acoustic impedance should not be used as the backing material 24. Instead the previous monolithic carrier for both the electronics body 12 and the transducer assembly 14 is replaced by the separated carrier/backing sections 20 and 24.

The continuous conducting electrode 44 covering the outer surface of the transducer material 40 is the ground plane for the transducer elements 22. It is preferably a layer of gold metal deposited upon the surface of the matching layer 46 by means of sputtering. However, other suitable conductors and methods to deposit the conductor will be known to those skilled in the art of transducers fabrication. Though not essential to the proper operation of the ultrasound catheter, it is preferred to connect in a known manner the continuous conducting electrode 44 to a ground line provided by the cable 28. The ground line runs along the electronics carrier 20 and is connected to the continuous conducting electrode after the electronics body 12 and the transducer assembly 14 have been joined. One possible way to connect the ground wire is shown in FIG. 2 of the Proudian, deceased et al. U.S. Pat. No. 4,917,097.

The transducer elements 22 are enclosed by a matching layer 46. As explained in *Biomedical Ultrasonics*, by P. N. T. Wells, Academic Press 1977, at page 54, the efficiency of transmission into the load may be increased by an impedance matching layer of quarter wavelength thickness. In the presently preferred embodiment the matching layer 46 comprises a loaded epoxy and is approximately 0.06 mm. thick. Alternative appropriate matching layer materials and their thicknesses will be apparent to those of ordinary skill in the art of ultrasonic imaging.

After independent construction, the electronics body 12 and the transducer assembly 14 are bonded together by a layer of glue 52 and the electrical connections between the electronics body 12 and the transducer assembly 14 are electrically coupled in a manner previously described. The cable 28 containing the leads from the signal processor for the ultrasound catheter (previously described in the Proudian et al. '097 patent) are bonded to the conductive pads 34 on the carrier 20 in a known manner.

FIG. 6 shows an alternative embodiment of the present invention, wherein the imaging device 10 is included in a diagnostic imaging catheter that does not contain a balloon 1. Portions of the diagnostic imaging catheter have been removed to reveal the cable 28 and the lumen 2. Since there is no balloon 1 in the imaging catheter shown in FIG. 6, there is of course no tube 26 for filling and draining a fluid from the balloon. Instead, the catheter is fitted with a nose cone 25. The nose cone 25 provides a blunted lead surface for the ultrasound imaging catheter in order to prevent damage to the walls of a cavity as the catheter is inserted. A sheath 38 covers the epoxy resin 8 thereby guarding against contamination of a patient's blood and possibly electrical shock. The sheath 38 is preferably constructed of parylene, though other suitable substitutes will be known to those skilled in the art of medical instruments that are inserted within a body. The structure of the imaging catheter shown in FIG. 6 is otherwise unchanged from the structure of the balloon angioplasty ultrasound imaging catheter illustrated in FIG. 1.

Though the preferred embodiment of the present invention contains a transducer array configured as a cylinder about a cylindrical core, there are numerous other configurations of ultrasound catheters that embody the present invention. Examples of such configurations are shown in FIGS. 7 and 8. Other configurations of transducer arrays for an ultrasound catheter will be known to those skilled in the art in view of the present description of this invention.

Figure 7A:
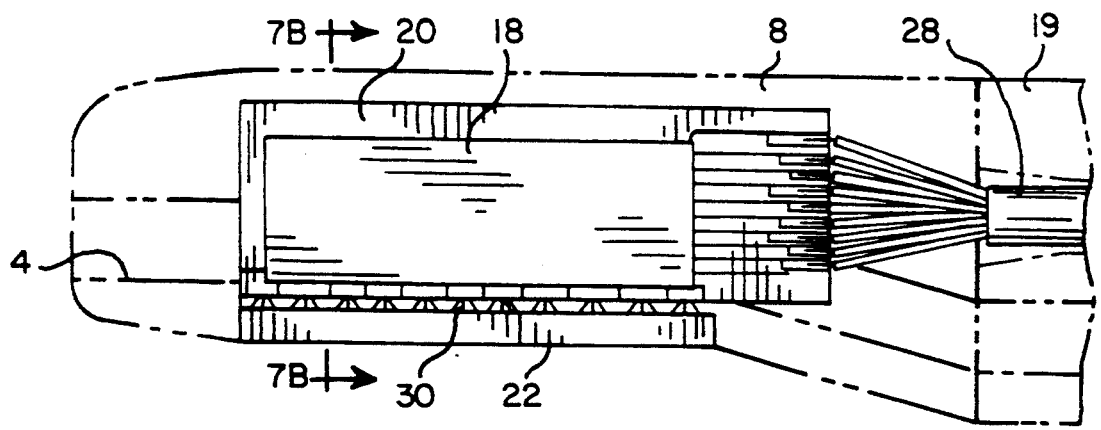
FIGS. 7a and 7b show cross-sectional and side-sectional views of an alternative embodiment of the present invention wherein the transducer array is configured to provide a "side-looking" view.
Figure 7B:
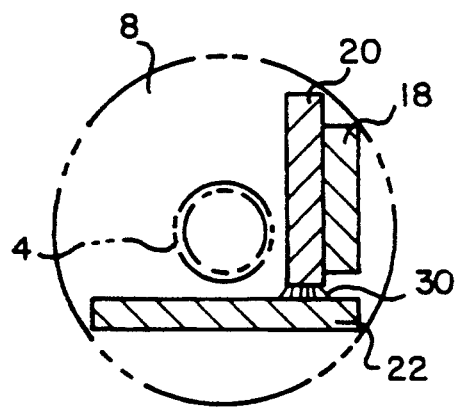

FIGS. 7A and 7B illustrate side and cross-sectional views of a side-looking linear array imaging catheter. In this arrangement the transducer elements 22 are arranged in a plane and perpendicular to the direction of insertion of the imaging catheter. This arrangement provides an image along the length of a cavity. In this alternative embodiment of the present invention, the IC's 18 are connected to the cable 28 in the same manner as the previously described embodiments of the invention. Furthermore, in accordance with the present invention, the IC's 18 are mounted upon an electronics carrier 20 of the type previously described in connection with the preferred embodiment of the invention shown in FIG. 1. The IC's are electrically coupled to the transducer elements 22 by conductor lines 30. The backing material for the transducer elements 22 forms the encapsulant 8 in this case.

Figure 8A:
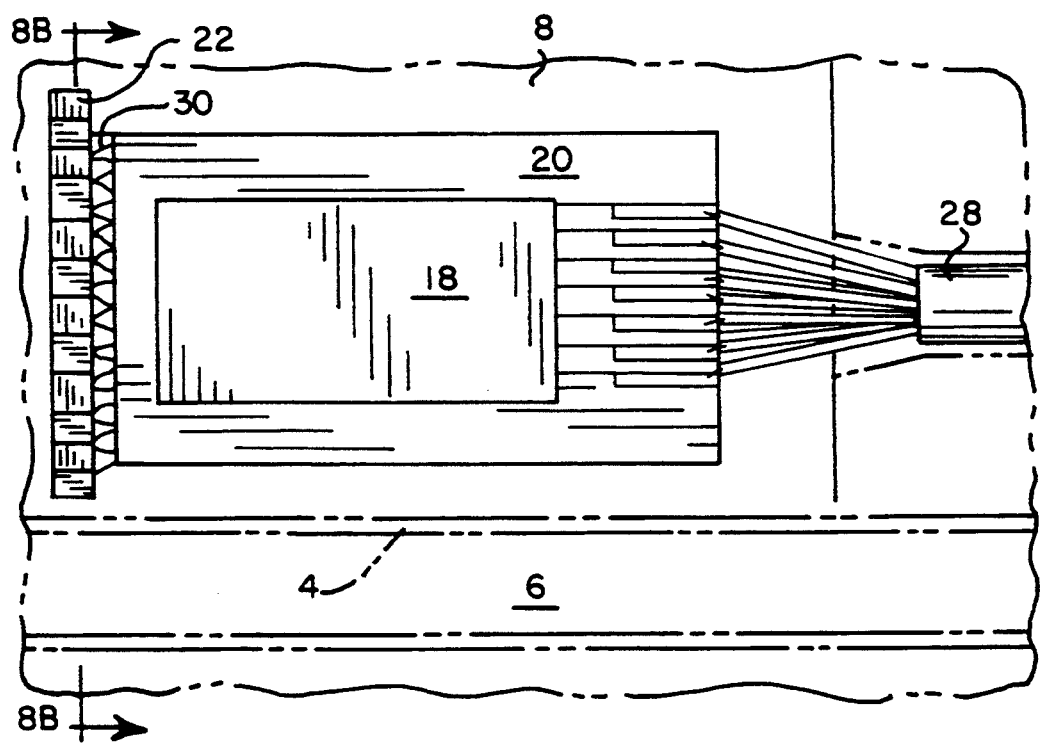
FIGS. 8a, 8b and 8c show side, forward, and top cross-sectional views of an alternative embodiment of the present invention wherein the transducer array is configured to provide a "forward-looking" view.
Figure 8B:
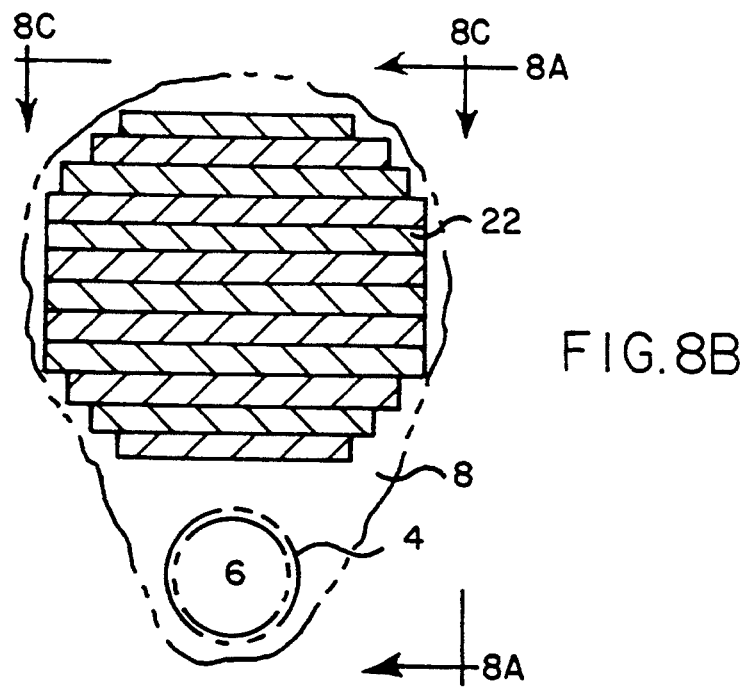
Figure 8C:
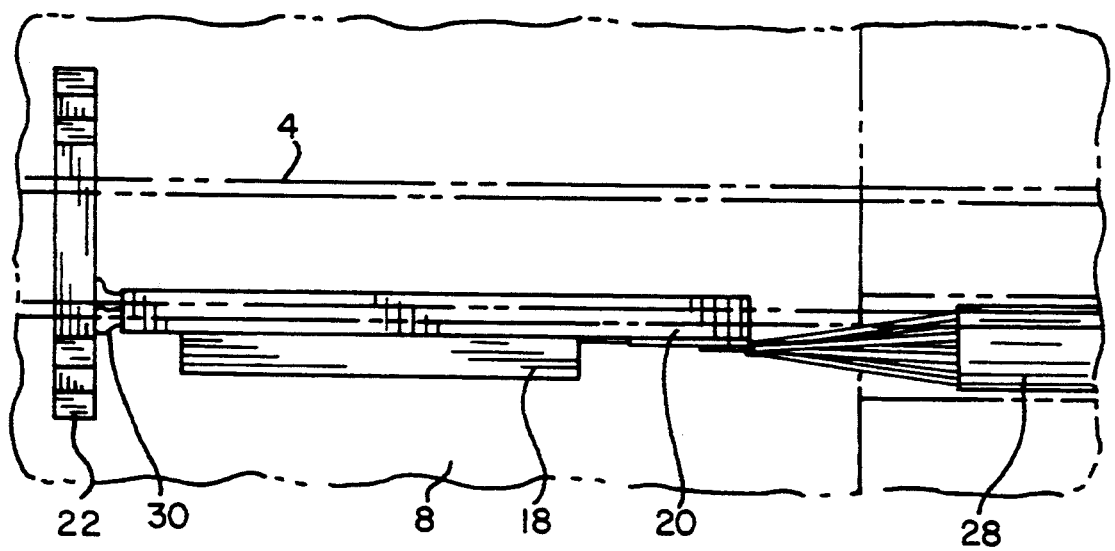

FIGS. 8A, 8B and 8C illustrate side, forward, and top cross-sectional views of a forward-looking "endfire" imaging catheter shown in FIG. 1. In FIGS. 8A, 8B and 8C the encapsulant 8, which is also the backing material for the transducers 22, has been partially removed to reveal the placement and orientation of the electronics portion. In this arrangement the transducer elements 22 are arranged as a planar array mounted upon the leading face of the catheter. The guide wire lumen 4 is mounted adjacent the ultrasonic imaging device. The diameter of the guide wire lumen 4 is approximately 0.3 mm or about one-third the diameter of the imaging catheter.

This arrangement provides a forward looking view of a cavity. The dimensions of the field of view are determined by the size of the array, the number of elements, the element dimensions and frequency. In this alternative embodiment of the present invention, the IC's 18 are connected to the cable 28 in the same manner as the previously described embodiments of the invention. Furthermore, in accordance with the present invention, the IC's 18 are mounted upon a carrier 20 of the type previously described in connection with the preferred embodiment of the invention shown in FIG. 1. The IC's are electrically coupled to the transducer elements 22 by conductor lines 30. The encapsulant 8 may form the backing material for the transducer elements 22.

It will be appreciated by those skilled in the art that modifications to the foregoing preferred embodiment may be made in various aspects. The present invention is set forth with particularity in the appended claims. It is deemed that the spirit and scope of that invention encompasses such modifications and alterations to the preferred embodiment as would be apparent to one of ordinary skill in the art and familiar with the teaching of the present application.

What is claimed is:

1. An ultrasound catheter probe for insertion into a vasculature and emitting ultrasonic acoustic waves and providing transduced electrical signals arising from ultrasonic echoes of the ultrasonic acoustic waves, said ultrasound catheter probe comprising:

a multi-sectioned body having distinct sections for independently supporting a transducer array and integrated electronic circuitry, the multi-sectioned body comprising:

a first section, comprising a first material, serving as a transducer backing and having a relatively high acoustic energy absorption in comparison to a second section, comprising a second material, for supporting integrated electronic circuitry;

a transducer assembly, mounted upon the first section of the multi-sectioned body, including the transducer array for transmitting the ultrasonic acoustic waves into the vasculature and generating first electrical signals in accordance with the ultrasonic echoes of the ultrasonic acoustic waves;

integrated electronic signal conversion circuitry, mounted upon the second section of the multi-sectioned body, for receiving the first electrical signals from the transducer assembly, converting the first electrical signals to second electrical signals, and transmitting the second electrical signals to an environment external of the vasculature via a cable including at least one signal channel for transmitting the second electrical signals; and a plurality of electrical transmission paths between the transducer array and the integrated electronic signal conversion circuitry for communicating the first electrical signals from the transducer array to the integrated electronic signal conversion circuitry.

2. The ultrasound catheter probe of claim 1 wherein the first section and the second section are mounted adjacently upon a guide wire lumen.

3. The imaging device of claim 1 wherein the first material has a relatively low acoustic impedance.

4. The imaging device of claim 1 wherein the second material has a relatively low thermal expansion coefficient in comparison to the first material.

5. The ultrasound catheter probe of claim 1 wherein the transducer assembly includes a plurality of conducting electrodes bonded directly to a transducer layer.

6. The ultrasound catheter probe of claim 1 wherein the transducer assembly includes a continuous layer conducting electrode bonded directly to a transducer layer.

7. The ultrasound catheter probe of claim 1 wherein the transducer assembly includes a transducer array configured in a cylindrical shape.

8. The ultrasound catheter probe of claim 1 wherein the transducer assembly includes a transducer array configured in a planar shape.

9. The ultrasound catheter probe of claim 8 wherein the transducer array is disposed upon a side of the multi-sectioned body in order to provide a side-looking view within the cavity.

10. The ultrasound catheter probe of claim 8 wherein the transducer array is disposed upon a front of the multi-sectioned body in order to provide a forward-looking view within the cavity.

11. The ultrasound catheter probe of claim 1 further comprising a balloon section positioned proximate the multi-sectioned body.

12. The ultrasound catheter probe of claim 11 wherein the balloon is positioned at a portion of a catheter which is inserted ahead of the multi-sectioned body.

13. The ultrasound catheter probe of claim 1 wherein said plurality of electrical transmission paths includes a set of transducer contacts coupled to a plurality of conducting electrodes of the transducer array and extending laterally from the transducer array thereby facilitating connection of the plurality of conducting electrodes to a plurality of conducting lines disposed upon the second section and electrically coupled to the integrated electronic signal conversion circuitry.

14. The ultrasound catheter probe of claim 13 wherein said set of transducer contacts overlap the plurality of conducting lines, thereby facilitating the use of a gap welder to fuse ones of the set of transducer contacts to corresponding ones of the plurality of conductor lines.

15. An ultrasound imaging catheter for insertion into a vasculature and emitting ultrasonic acoustic waves and providing transduced electrical signals arising from ultrasonic echoes of the ultrasonic acoustic waves, said imaging catheter comprising:
   a shaft containing at least one lumen; and
   an ultrasound probe mounted upon the shaft, said imaging device comprising:
      a multi-sectioned body having distinct sections for independently supporting a transducer array and integrated electronic circuitry, the multi-sectioned body comprising:
         a first section, comprising a first material, serving as a transducer backing and having a relatively high acoustic energy absorption in comparison to a second section, comprising a second material, for supporting integrated electronic circuitry;
      a transducer assembly, mounted upon the first section of the multi-sectioned body, including the transducer array for transmitting the ultrasonic acoustic waves into the vasculature and generating first electrical signals in accordance with the ultrasonic echoes of the ultrasonic acoustic waves;
      integrated electronic signal conversion circuitry, mounted upon the second section of the multi-sectioned body, for receiving the first electrical signals from the transducer assembly, converting the first electrical signals to second electrical signals, and transmitting the second electrical signals to an environment external of the vasculature via a cable including at least one signal channel for transmitting the second electrical signals; and
      a plurality of electrical transmission paths between the transducer array and the integrated electronic signal conversion circuitry for communicating the first electrical signals from the transducer array to the integrated electronic signal conversion circuitry.

16. A method for assembling an ultrasound intravascular catheter probe having a multi-sectioned body for independently supporting a transducer array and integrated electronic circuitry, the multi-sectioned body having a first section consisting of a transducer backing and a second section for supporting the integrated electronic circuitry, said method comprising the steps of:
   mounting upon the first section of the multi-sectioned body a transducer assembly including the transducer array for transmitting ultrasonic acoustic waves into the vasculature and generating first electrical signals in accordance with ultrasonic echoes of the ultrasonic acoustic waves, said transducer assembly including a set of transducer contacts coupled to a plurality of conducting electrodes and extending laterally from the transducer array;
   mounting upon the second section of the multi-sectioned body integrated electronic signal conversion circuitry for receiving the first electrical signals from the array of transducers and converting the first electrical signals to second electrical signals transmitted by a cable connecting the integrated electronic signal conversion circuitry to an environment external of the vasculature and including at least one signal channel for transmitting the second electrical signals;
   bringing the first and second sections in proximate position so that ones of the set of transducer contacts overlap corresponding ones of a set of conductor lines communicatively connected to the integrated electronic signal conversion circuitry; and
   applying a localized electrical current source to overlapping transducer contacts and conductor lines, thereby fusing ones of the transducer contacts to ones of the conductor lines.

17. The method of claim 16 wherein the applying step comprises applying localized electrical current to each of the overlapping transducer contacts and conductor lines by means of a gap welder.

* * * * *